United States Patent [19]
Alak et al.

[11] Patent Number: 5,563,059
[45] Date of Patent: Oct. 8, 1996

[54] USE OF HUMAN INHIBIN AND HUMAN ACTIVIN TO INCREASE THE NUMBER OF MATURE PRIMATE OOCYTES

[75] Inventors: Baha M. Alak, Beaverton; Richard L. Stouffer, Aloha; Don P. Wolf, Portland, all of Oreg.; Teresa K. Woodruff, San Francisco, Calif.

[73] Assignees: Genentech, Inc., South San Francisco, Calif.; Medical Research Foundation of Oregon, Beaverton, Oreg.

[21] Appl. No.: 21,404

[22] Filed: Feb. 23, 1993

[51] Int. Cl.$^6$ .............................. C12N 5/00; A01N 1/02; A61B 17/435; A61K 38/00; A61K 38/16; A61K 35/48; A61K 35/52; A61K 35/54

[52] U.S. Cl. .................................. 435/240.2; 435/240.3; 435/2; 600/33; 600/34; 514/8; 514/12; 514/21; 424/93.7; 424/559; 424/561

[58] Field of Search .............................. 435/240.2, 240.3, 435/2; 600/33, 34; 514/21, 12, 8; 424/559, 561, 93.7

[56] References Cited

U.S. PATENT DOCUMENTS

| | | | |
|---|---|---|---|
| 4,845,077 | 7/1989 | Hodgen | 514/2 |
| 5,102,868 | 4/1992 | Woodruff et al. | 514/8 |
| 5,166,190 | 11/1992 | Mather et al. | 514/8 |
| 5,206,160 | 4/1993 | Takahashi et al. | 435/189 |

FOREIGN PATENT DOCUMENTS

| | | |
|---|---|---|
| 0340934 | 11/1989 | European Pat. Off. . |
| 0417743 | 3/1991 | European Pat. Off. . |
| 0521674 | 1/1993 | European Pat. Off. . |
| WO90/13627 | 11/1990 | WIPO . |
| WO91/10445 | 7/1991 | WIPO . |

OTHER PUBLICATIONS

Byrd, "Gamete Intrafallopian Transfer (Gift)", *In Vitro Fertilization and Embryo Transfer: A manual of basic techniques* (D. P. Wolf, ed.), Plenum Press, 265–279, (1988).
Gerrity et al., "Embryo Transfer", *In Vitro Fertilization and Embryo Transfer: A manual of basic techniques* (D. P. Wolf, ed.), Plenum Press, 189–207, (1988).
Malloy et al., "A laparoscopic approach to a program of gamete intrafallopian transfer", *Fertil. Steril.*, 47(2):289 (1987).
Quigly et al., "Follicular size and number in human in vitro fertilization", *Fertil. Steril.*, 38(6):678 (1982).
Yovich et al., "Pregnancies following pronuclear stage tubal transfer", *Fertil. Steril.*, 48(5):851–857, (1987).
Hutchinson et al., BBRC, 146(3):1405–1412 (1987), "Effects of Bovine Inhibin, Transforming Growth Factor–β and Bovine Activin–A on Granulosa Cell Differentiation".
Ying et al., BBRC, 136(3):969–975 (1986), "Inhibin and Beta Type Transforming Growth Factor have Opposite Modulating Effects on the Follicle Stimulating Hormone (FSH)–Induced Aromatase Activity . . . ".
Adashi & Resnick, Endocrinol., 119(4):1879–1881 (1986), "Antagonistic Interactions of Transforming Growth Factors in the Regulation of Granulosa Cell Differentiation".

Ignotz & Massague, J. Biol. Chem., 261(9):4337–4345 (1986), "Transforming Growth Factor–β Stimulates the Expression of Fibronectin and Collagen and Their Incorporation into the Extracellular Matrix".
deKretser & Robertson, Biol. of Reprod., 40:33–47 (1989), "The Isolation and Physiology of Inhibin and Related Proteins".
Hsueh et al., PNAS USA, 84:5082–5086 (1987), "Heterodimers and Homodimers of Inhibin Subunits have Different Paracrine Action in the Modulation of Luteinizing Hormone–Stimulated Androgen Biosynthesis".
Hillier et al., J. Clin. Endocr. Metab., 72(6):1206–1211 (1991), "Effect of Recombinant Activin on Androgen Synthesis in Cultured Human Thecal Cells".
Hillier et al., Mol. Cell. Endocr., 75:R1–R6 (1991), "Effect of Recombinant Inhibin on Androgen Synthesis in Cultured Human Thecal Cells".
Bramley et al., J. Endocrin., 134:341–352 (1992), "Apparent α–inhibin subunit immunoactivity in porcine and ovine luteal extracts is due to interference by cytosolic proteases in the assay".
McLachlan et al., Fert. and Steril., 48(6):1001–1005 (1987), "Circulating immunoactive Inhibin in the Luteal Phase and Early Gestation of Women Undergoing Ovulation Induction".
Lee et al., Science, 243:396–398 (1989), "Secretion of Activin by Interstitial Cells in the Testis".
Mitrani et al., Cell, 63:495–501 (1990), "Activin can induce the formation of axial structures and is expressed in the hypoblast of the chick".
Mather et al., Endocrin., 127:3206–3214 (1990), "Activin stimulates spermatogonial proliferation in germ–sertoli cell cocultures from immature rat testis".
Smith et al., Nature, 345:729–731 (1990), "Identification of a potent xenopus mesoderm–inducing factor as a homologue of activin A".
Sugino et al., BBRC, 153:281–288 (1988), "Erythroid differentiation factor can modulate follicular granulosa cell functions".
Whittemore et al., Am. J. Epidemiol., 136:1184–1203 (1992), "Characteristics relating to ovarian cancer risk: Collaborative analysis of 12 US case–control studies".
Sathananthan et al. in Ultrastructure of the Ovary, Familiari et al., eds., Kluwer Academic Publ., Norwell, MA 1991, pp. 29–43, "Maturation of the human oocyte".

(List continued on next page.)

*Primary Examiner*—Michael G. Wityshyn
*Assistant Examiner*—Susan M. Dadio
*Attorney, Agent, or Firm*—Janet E. Hasak

[57] ABSTRACT

A method is provided for increasing the fertilization potential of oocytes comprising culturing oocytes in vitro with an effective amount of inhibin, activin, or a combination of inhibin and activin. Preferably the oocytes being cultured are immature. After the culturing step, the oocytes can be fertilized. The oocytes are suitably cryopreserved and thawed before the culturing step.

18 Claims, 6 Drawing Sheets

Lee et al. in The Molecular and Cellular Endocrinology of the Testis, Serono Symposia Publications from Raven Press, Cooke et al., eds., 1988, 50: 21–27, "Interstitial Cell Cultures Secrete and Activity with . . .".

Lee and Gibson, Aust. J. Biol. Sci., 38:115–120 (1985), "Ovulation Rate and Inhibin Levels in Gonadotrophin-treated mice".

Baird et al., Ann. NY. Acad. Sci., 541:153–161 (1988), "Inhibin Levels in Gonadotropin–Treated Cycles".

Sheth et al., Adv. Contracept., 2:131–139 (1986), "Potential Application of Inhibin in Male and Female Contraception".

Franchimont et al., Rev. Fr. Gynecol. Obstet, 83(10):607–611 (1988), "Inhibin and Related Peptides: Mechanisms of Action and Regulation of Secretion".

Woodruff et al. in Growth Factors and the Ovary, Hirshfield, ed., Plenum Press, NY (1989), 291–295, "Modulation of Rat Inhibin mRNAs in Preovulatory and Atretic Follicles".

Osborn et al., J. Reprod. Fert., Suppl. 36:59–72 (1988), "An assessment of the factors causing embryonic loss after fertilization in vitro".

Sathananthan et al. in Ultrastructure of human gametogenesis and early embryogenesis, van Blerkom et al., eds., Kluwer Academic Publishers, 1989, pp. 181–199, "Effects of culture and cryopreservation on human oocyte . . .".

Trounson in Clinical in vitro fertilization, 2nd Ed., Wood et al., eds., Springer–Verlag, 1989, pp. 33–50, "Fertilization and embryo culture".

Trounson in Clinical in vitro fertilization, 2nd Ed., Wood et al., eds., Springer–Verlag, 1989, pp. 127–142, "Embryo cryopreservation".

Trounson et al., J. Reprod. Fert., 64:285–294 (1982), "Effect of delayed insemination on in–vitro fertilization, culture and transfer of human embryos".

Al–Obaidi et al., J. Reprod. Fert., 81:403–414 (1987), "Reproductive Charracteristics of Lambs Actively Immunized Early in Life with Inhibin–enriched Preparations from Follicular Fluid of Cows".

Cummins et al., J. Reprod. Fert., 77:365–372 (1986), "Increase in Ovulation rate After Immunization of Merino Ewes with a Fraction of Bovine Follicular Fluid Containing Inhibin Activity".

Bremner et al., J. Clin. Invest., 68:1044–1052 (1981), "Follicle–Stimulating Hormone and Human Spermatogenesis".

Henderson et al., J. Endocrin., 102:305–309 (1984), "Increase in Ovulation Rate After Active Immunization of Sheep with Inhibin Partially Purified from Bovine Follicular Fluid".

Forage et al., J. Endocrin., 114:R1–R4 (1987), "Immunization Against an Inhibin Subunit Produced by Recombinant DNA Techniques Results in Increased Ovulation Rate in Sheep".

Sathananthan et al., Gamete Res., 5:191–198 (1982), "Ultrastructural observations on cortical granules in human follicular oocytes cultured in vitro".

Baker et al., Clin. Reprod. and Fert., 2:161–174 (1983), "Present Status of Research on Inhibin: An Appraisal".

Hasegawa et al. in Inhibin–non–steroidal regulation of follicle stimulating hormone secretion, Serono Publ., Raven Press, Burger et al., eds., 42:119–133 (1987), "Changes in serum concentrations of inhibin during the . . .".

Sathananthan et al., Gamete Res., 16:343–354 (1987), "Morphology and Fertilizability of Frozen human oocytes".

Lefevre et al., Fert. and Steril., 46(2):325–327 (1986), "Absence of Predictive Value of Follicular Inhibin on the Results of Human in vitro Fertilization".

Al–Hasani et al., Human Reprod., 2:695–700 (1987), "Cryopreservation of human oocytes".

Findlay, Fertil. and Steril., 46(5):770–783 (1986), "The Nature of Inhibin and its Use in the Regulation of Fertility and Diagnosis of Infertility".

Woodruff et al., Science, 239:1296–1299 (1988), "Dynamic Changes in Inhibin Messenger RNAs in Rat Ovarian Follicles During the Reproductive Cycle".

Woodruff et al., Endocrin., 124:2193–2199 (1989), "Decreased inhibin gene expression in preovulatory follicles requires primary gonadotropin surges".

Rivier et al., Science, 234:205–208 (1986), "Inhibin–mediated feedback control of follicle–stimulating hormone secretion in the female rat".

D'Agostino et al., Endocrin., 124:310–317 (1989), "Unilateral ovariectomy increase inhibin messenger ribonucleic acid levels in newly recruited follicles".

DePaolo et al., Proc. Soc. Exp. Biol. & Med., 198:500–512 (1991), "Follistatin and activin: A potential intrinsic regulatory system within diverse tissues".

Mondschein et al., Endocrin., 123(4):1970–1976 (1988), "Effects of Transforming Growth Factor–$\beta$ on the Production of Immunoreactive Insulin–Like Growth Factor I and Progesterone and on . . .".

Feng et al., J. Biol. Chem., 261(30):14167–14170 (1986), "Transforming Growth Factor $\beta$ Regulates the Inhibitory Actions of Epidermal Growth Factor During Granulosa Cell Differentiation".

Carson et al., J. Reprod. Fert., 85:735–746 (1989), "Growth Factors in Ovarian Function".

Zhiwen et al., Mol. Cell. Endocrin., 58:161–166 (1988), "Transforming growth factor $\beta$ enhances basal and FSH–stimulated inhibin production by rat granulosa cells in vitro".

Gonzalez–Manchon and Vale, Endocrin., 125(3):1666–1672 (1989), "Activin–A, Inhibin and Transforming Growth Factor–$\beta$ Modulate Growth of Two Gonadal Cell Lines".

de Jong, Physiol. Rev., 68(2):555–607 (1988), "Inhibin".

Stouffer et al., J. Clin. Endocrin., In Press, (Jul. 1993), "Human Recombinant Activin–A Alters Pituitary LH and FSH Secretion, Follicular Development, and Steroidogenesis, During the Menstrual Cycle in Rhesus Monkeys".

Sathananthan et al., Human Reprod., 3:968–977 (1988), "The effects of cooling human oocytes".

van Blerkom, Human Reprod., 4:883–898 (1989), "Maturation at high frequency of germinal–vesicle–stage mouse oocytes after cryopreservation: . . .".

Pickering et al., Fert. Steril., 54:102–108 (1990), "Transient cooling to room temperature can cause irreversible disruption of the meiotic spindle in the human oocyte".

Trounson et al., Developments in Ultrastructure of Reproduction, 1989, Alan R. Liss, Inc., pp. 355–366, "Human oocyte and embryo freezing".

Cha et al., Fert. Steril., 55:109–113 (1991), "Pregnancy aftre in vitro fertilization of human follicular oocytes collected from nonstimulated cycles, their culture in vitro and their transfer in a donor oocyte program".

O et al., Mol. Cell. Endocrin., 62:307–311 (1989), "Inhibin as an oocyte meiotic inhibitor".

Itoh et al., BBRC, 166:1479–1484 (1990), "Activin A stimulates meiotic maturation of the rat oocyte in vitro".

Tsuchiya et al., Fert. and Steril., 52(1):88–94 (1989), "Correlation of Serum Inhibin Concentrations with Results in an Ovarian Hyperstimulation Program".

Buckler et al., J. Endocrinol., 122:279–285 (1989), "Purified FSH Stimulates Production of Inhibin by the Human ovary".

Tsonis et al., J. Clin. Endocrin. and Metab., 66(5):915–921 (1988), "Gonadotropic Stimulation of Inhibin Secretion by the Human Ovary During the Follicular and Early Luteal Phase of the Cycle".

McLachlan et al., The Lancet, May 31, 1986, 1233–1234, "Plasma Inhibin Levels During Gonadotropin-Induced Ovarian Hyperstimulation for IVF: A New Index of Follicular Function?".

Trounson et al., Science, 212:681–682 (1981), "Pregnancies in human by fertilization in vitro and embryo transfer in the controlled ovulatory cycle".

Rivier and Vale, Endocrin., 125(1):152–157 (1989), "Immunoneutralization of Endogenous Inhibin Modifies Hormone Secretion and Ovulation Rate in the Rat".

Robertson et al., "Inhibin as an Oocyte Meiotic Inhibitor", *Mol. and Cell. Endocrin.*, 62:307–311, (1989).

USE OF HUMAN INHIBIN AND HUMAN ACTIVIN TO INCREASE THE NUMBER OF MATURE PRIMATE OOCYTES

BACKGROUND OF THE INVENTION

1. Field of the Invention

This invention relates to an in vitro method for enhancing the potential of oocytes to be fertilized.

2. Description of Related and Background Art

Inhibin and activin are members of a family of growth and differentiation factors. The prototype of this family is transforming growth factor-beta (TGF-β). Derynck et al., *Nature*, 316: 701–705 (1985); Ying et al., *Biochem. Biophys. Res. Commun.*, 135: 950–956 (1986). Other members of the TGF-β family include the Mullerian inhibitory substance, the fly decapentaplegic gene complex, and the product of Xenopus Vg-1 mRNA.

Inhibin is a glycoprotein produced by diverse tissues, including the gonads, pituitary, brain, bone marrow, placenta, and adrenal gland. It was initially identified by its ability to inhibit the secretion of follicle stimulating hormone (FSH) by the pituitary. De Jong and Sharpe, *Nature*, 263: 71–72 (1976); Schwartz and Channing, *Proc. Natl. Acad. Sci. USA*, 74: 5721–5724 (1977). Such preferential regulation of the gonadotropin secretion has generated a great deal of interest and prompted many laboratories in the past fifty years to attempt to isolate and characterize this substance from extracts of testis, spermatozoa, rete testis fluid, seminal plasma, and ovarian follicular fluid using various bioassays. Rivier et al., *Biochem. Biophys. Res. Commun.*, 133:120 (1985); Ling et al., *Proc. Natl. Acad. Sci. USA*, 82: 7217 (1985); Fukuda et al., *Mol. Cell Endocrinol.*, 44:55 (1985). The structure of inhibin, characterized from several species, consists of two disulfide-linked subunits: an α and either a $β_A$ or a $β_B$ chain.

After the identification of inhibin, activin was shown to exist in follicular fluid as a naturally occurring substance. Activin was found to be capable of stimulating FSH release by rat anterior pituitary cells. Vale et al., *Nature*, 321: 776–779 (1986); Ling et al., *Nature*, 321: 779–782 (1986); DePaolo et al., *Pro. Soc. Exp. Biol. Med.*, 198: 500–512 (1991); Ying, *Endocrine Rev.*, 9: 267–293 (1988). Recombinant activin was also found to stimulate pituitary LH and FSH in the adult male macaque. McLachlan et al., *Endocrinol.*, 125: 2787–2789 (1989). Activin consists of a homodimer or heterodimer of inhibin β subunits, which may be $β_A$ or $β_B$ subunits. Vale et al., *Recent Prog. Horm. Res.*, 44: 1–34 (1988). There is 95–100% amino acid conservation of β subunits among human, porcine, bovine, and rat activins including the prepro region. The $β_A$ and $β_B$ subunits within a given species are about 64–70% homologous.

The inhibin heterodimers $αβ_A$ and $αβ_B$ ("Inhibin A" and "Inhibin B," respectively) and the activin $β_A$ and $β_B$ homodimers ("Activin A" and "Activin B," respectively) have been identified in and purified from follicular fluid, and all these molecules have been cloned and their genes expressed. Mason et al., *Biochem. Biophys. Res. Commun.*, 135:957 (1986); U.S. Pat. No. 4,798,885 issued Jan. 17, 1989; Mason et al., *Molecular Endocrinol.*, 3: 1352–1358 (1989); Schwall et al., *Mol. Endocrinol.*, 2: 1237–1242 (1988); Nakamura et al., *J. Biol. Chem.*, 267: 16385–16389 (1992). The complete sequence of the $β_B$ subunit is published in Serono Symposium Publications, entitled "Inhibin-Non-Steroidal Regulation of Follicle Stimulating Hormone Secretion," eds. Burger et al., abstract by Mason et al., vol. 42, pp. 77–88 (Raven Press, 1987), entitled "Human Inhibin and Activin: Structure and Recombinant Expression in Mammalian Cells." The recombinant activin molecule has been shown to increase serum levels of FSH in rats when delivered by subcutaneous injection. Schwall et al., *Endocrinol.*, 125: 1420–1423 (1989); Rivier and Vale, *Endocrinol.*, 129: 2463–2465 (1991).

Activin and inhibin regulate the growth and functions of a variety of cell types. They may be involved in diverse biological processes including erythropoiesis, bone formation, placental and gonadal steroidogenesis, neuronal survival, and embryologic mesodermal induction. In addition, activin has an effect on follicular granulosa cell differentiation (Sugino et al., *Biochem. Biophys. Res. Commun.*, 153: 281–288 [1988]), spermatogonial proliferation (Mather et al., *Endocrinol.*, 127: 3206–3214 [1990]), erythroid differentiation (EP Publ. No. 210,461 published Feb. 4, 1987 [where the protein is called BUF-3]; Eto et al., *Biochem. Biophys. Res. Commun.*, 142: 1095–1103 [1987] and Murata et al., *Proc. Natl. Acad. Sci. USA*, 85: 2434–2438 [1988] [where the activin is called EDF]; Yu et al., *Nature*, 330: 765–767 [1987] [where the activin is called FRP]), stimulation of insulin secretion by pancreatic islets (Totsuka et al., *Biochem. Biophys. Res. Commun.*, 156: 335–339 [1988]), enhancement of proliferation of fibroblast (Hedger et al., *Mol. Cell. Endocrinol.*, 61: 133–138 [1989]), stimulation of glucose production by hepatocytes (Mine et al., *Endocrinology*, 125: 586–591 [1989]), induction of a dose-dependent increase in inositol phosphates in rat parenchymal liver cells, an effect also seen with EGF (Mine et al., *Biochem. Biophys. Res. Comm.*, 186: 205–210 [1992]), modulation of somatotroph functions (Billestrup et al., *Mol. Endocrinol.*, 4: 356–362 [1990]), modulation of nerve cell differentiation (Schubert et al., *Nature*, 344: 868–870 [1990]; Hashimoto et al., *Biochem. Biophys. Res. Comm.*, 173:193–200 [1990]), and mesoderm induction. Smith et al., *Nature*, 345: 729–731 (1990); Mitrani et al., *Cell*, 63: 495–501 (1990).

The expression of inhibin subunits, each encoded by a separate gene, was demonstrated in several tissues in addition to ovary. Woodruff et al., *Molec. Endocrinol.*, 1: 561–568 (1987). Inhibin α, $β_A$, and $β_B$ mRNAs were detected in testis, placental, pituitary, adrenal, bone marrow, and brain tissues. Meunier et al., *Proc. Natl. Acad. Sci. USA*, 85: 247–251 (1988). The expression of the inhibin subunit mRNAs varied by several-fold in a tissue-specific manner, suggesting different functions for these proteins depending on their pattern of association and their site of production. Activin mRNA ($β_A$ and $β_B$ subunits), bioactivity, and immunoactivity have been reported to be produced by testicular Leydig cells from immature rat and pig. Lee et al., *Science*, 243: 396–398 (1989); Lee et al., in Serono Symposium Publications, entitled "The Molecular and Cellular Endocrinology of the Testis" eds. Cooke and Sharpe, Vol. 50 (Raven Press: New York, 1988), p. 21–27.

A new class of gonadal protein factors, named follistatin or FSH-suppressing protein (FSP), was isolated from side fractions derived from purifying porcine and bovine ovarian inhibins and activins. Ying, *Endoc. Rev.*, 9: 267–293 (1988); Ling et al., "Isolation and characterization of gonadal polypeptides that regulate the secretion of follicle stimulating hormone," in Hodgen et al., eds., *Non-Steroidal Gonadl Factors: Physiological Roles and Possibilities in Contraceptive Development*, Jones Institute Press, Virginia, (1988), pp. 30–46. Follistatin was initially characterized by its ability to suppress FSH secretion from the pituitary. Thus, one biologic effect of follistatin is apparently similar to that of inhibin, but structurally the two proteins are quite different. Ueno etal., *Proc. Natl. Acad. Sci. USA*, 84: 8282–8286 (1987); Robertson et al., *Biochem. Biophys. Res. Commun.*, 149: 744–749 (1987).

Follistatin is a glycosylated single-chain protein that is found in forms having molecular weights ranging from 31 to 39 kDa. All of these forms have similar amino acid compositions and identical amino-terminal amino acid sequences. The molecular cloning of cDNA with the gens of follistatin revealed two forms, a smaller molecular weight form and a larger form, which are generated by alternative splicing. The smaller form represents a carboxy-terminal truncated form of the larger precursor. For a review on follistatin and activin, see DePaolo et al., *Proc. Soc. Exp. Biol. and Med.*, 198: 500–512 (1991). Follistatin is now thought to be an inhibin/activin binding protein.

In the human, growing preovulatory follicles and the corpus luteum secrete inhibin into the circulation in response to FSH stimulation. Lee and Gibson, *Aust. J. Biol. Sci.*, 38: 115–120 (1985); McLachlan et al., *Fertil. Steril.*, 48: 1001 (1987). Thus, inhibin-related peptides play important roles in the modulation of gonadal functions via a pituitary feedback loop. The secretion of inhibin by the corpus luteum has been proposed to suppress the concentration of FSH in the luteal phase of the cycle and hence the inhibition of follicular development. Baird et al., *Ann. N. Y. Acad. Sci.*, 541: 153–161 (1988). However, recent data suggest that the corpus luteum does not secrete inhibin. Bramley et al., *J. Endocrinol.*, 134: 341–352 (1992).

In primary cultures of rat testis cells and ovarian the calinterstitial cells, inhibin is reported to enhance androgen biosynthesis stimulated by luteinizing hormone (LH) (Hillier et al., *Mol. Cell. Endocrinol.*, 75: R1–R6 [1991]), whereas activin suppresses androgen production. Hillier et al., *J. Clin. Endocrinol. Metabol.*, 72: 1206–1211 (1991); Hsueh et al., *Proc. Natl. Acad. Sci. USA*, 84: 5082–5086 (1987). Other workers have been unable to repeat these observations in the male. deKretser and Robertson, *Biol. Reprod.*, 40: 33–47 (1989).

Inhibitory effects of TGF-β on Leydig cell steroidogenesis have also been described. Lin et al., *Biochem. Biophys. Res. Commun.*, 146: 387 (1987); Fauser and Hsueh, *Life Sci.*, 43: 1363 (1988); Avallet et al., *Biochem. Biophys. Res. Commun.*, 146: 575 (1987). In granulosa cells, activin has been reported to inhibit (and TGF-β to enhance) progesterone production. Ignotz and Massague, *J. Biol. Chem.*, 261: 4337 (1986). In primary cultures of granulosa cells, activin and inhibin as well as TGF-β were found to affect hormone synthesis and secretion, each in a different fashion. Adashi and Resnick, *Endocrinology*, 119: 1879 (1986); Ying et al., *Biochem, Biophys. Res. Commun.*, 136: 969 (1986); Hutchinson et al., *Biochem. Biophys. Res. Commun.*, 146: 1405 (1987); Mondschein et al., *Endocinology*, 123: 1970 (1988); Feng et al., *J. Biol. Chem.*, 261: 14167 (1986). These molecules have both positive and negative effects on FSH-dependent granulosa cell function. Carson et al., *J. Reprod. Fert.*, 85: 735–746 (1989). Also suggested is that individual members of the TGF-β/inhibin gene family regulate ovarian function, not only by direct action on follicle cells, but also indirectly by influencing the production rate of other members of that family. Zhiwen et al., *Molecular and Cellular Endocrinology*, 58: 161–166 (1988).

Activin and inhibin were reported to modulate growth of two gonadal cell lines, suggesting that these proteins may regulate proliferation as well as functions of gonadal cells. Gonzalez-Manchon and Vale, *Endocrinology*, 125: 1666–1672 (1989).

A review article postulates that inhibin is at least one of the factors that determines the number of follicles destined to ovulate, and that interference with the action of inhibin might contribute to the regulation of fertility. De Jong, *Physiol. Rev*, 68: 555 (1988). Many investigators have speculated that due to its FSH-inhibiting effect at the level of the pituitary, inhibin may be useful in male and female contraception. Sheth and Moodbidri, *Adv. Contracept.* 2: 131–139 (1986); Findlay, *Fertil. Steril.*, 46: 770 (1986). Another author doubts that inhibin can inhibit spermatogenesis (citing Bremner et al., *J. Clin. Invest.*, 68: 1044 [1981]), and states that inhibin might also have some direct stimulatory effects on spermatogenesis. Baker et al., *Clin. Reprod. and Fert.*, 2: 161–174 (1983). It has now been shown that inhibin has a paracrine effect in stimulating ovarian follicular maturation. WO 91/10445.

When sheep are immunized with inhibin or the inhibin α chain, their ovulation rate is increased, due to the immunoneutralization of endogenous inhibin. Cummins et al., *J. Reprod. Fertil.*, 77: 365 (1986); Henderson et al., *J. Endocrinol.*, 102: 305–309 (1984); Forage et al., *J. Endocrinol.*, 114: R1 (1987); Al-Obaidi et al., *J. Reprod. Fert.*, 81: 403–414 (1987). The same effect has been observed in rats. Rivier and Vale, *Endocrinology*, 125: 152 (1989). In addition, Rivier and Vale suggest that increased FSH alone is sufficient to stimulate additional follicular growth and development, and the main mechanism through which treatment with anti-inhibin serum increases follicular development is through elevated plasma FSH levels. Other investigators reported that the administration of inhibin to sheep induces either anovulation or an increase in ovulation rate according to the scheme of treatment. Franchimont et al., *Rev. fr. Gynecol. Obstet.*, 83: 607 (1988).

Activin is disclosed as useful for treating male infertility (see U.S. Pat. No. 5,166,190) and for treating polycystic ovarian disease when administered directly to the ovary. U.S. Pat. No. 5,102,868.

The modulation of the inhibin subunit mRNAs during the rat estrous cycle has been intensely studied. Woodruff et al., *Science*, 239: 1296 (1988). Only recently has the integrative feedback relationship between ovarian inhibin and activin and pituitary FSH been partially elucidated. Hasegawa et al., in *Inhibin: Non-Steroidal Regulation of FSH Secretion*, ed. J. Burger et al., 42: 119–133 (New York: Raven Press, 1987); Woodruff et al., *Science*, 239: 1296–1299 (1988). Briefly, the ovary produces low levels of inhibin on the evening of proestrus. Woodruff et al., *Endocrinol.*, 2193–2199 (1989). This allows FSH to remain elevated throughout the morning of estrus (secondary FSH surge). Rivier et al., *Science*, 234: 205–208 (1986). The secondary FSH surge recruits a new set of follicles into the ovulatory pool and is responsible for the initiation of inhibin subunit mRNA expression. D'Agostino et al., *Endocrinol.*, 124: 310–317 (1989). As a consequence of inhibin production, pituitary FSH secretion is downregulated. Inhibin mRNA levels increase in maturing follicles as they progress through the cycle. Follicles that become atretic (non-ovulatory and highly steroidogenic) have little or no inhibin mRNA. Woodruff et al., in *Growth Factors and the Ovary*, ed. Hirshfield, pp. 291–295 (New York: Plenum Press, 1989). Inhibin subunit mRNA accumulation climaxes on the afternoon of proestrus in healthy follicles simultaneously with the primary LH and FSH surges. Woodruff et al., *Science*, supra.

For maturation within their normal follicular environment, oocytes need to acquire meiotic competence but remain in meiotic arrest of prophase until stimulated to resume meiosis by the preovulatory gonadotropin surge. The oocyte becomes developmentally competent within a few hours of ovulation, having progressed to metaphase II (MII) and undergoing changes in metabolism, synthesis of proteins, and redistribution of cytoplasmic organelles. Sathananthan et al., "Maturation of the human oocyte," in *Ultastructure of the Ovary*, Familiari et al. (eds.) (Morwell, MA: Kluwer Academic Publishers, 1991), Chapter 2, pp. 29–43.

Oocyte maturation is necessary for successful in vitro fertilization (IVF). The stages of preovulatory maturation range from the immature germinal vesicle (GV) stage to MII of meoisis. The maturation includes both nuclear and cytoplasmic maturation of the germ cell.

Since the first successful IVF procedure in 1978, attempts have been made to employ drugs or hormones to induce multiple follicular and oocyte development. Thus, IVF pregnancies could result in women following the use of clomiphene citrate and human chorionic gonadotrophin (hCG) to induce multiple follicular development in endocrine normal patients. Trounson et al., *Science*, 212: 681–684 (1981). It is well established that the appropriate application of mixed exogenous gonadotropins FSH and LH has proven efficacious for ovulation induction or for multiple egg retrieval during IVF therapy. However, ovarian and oocyte stimulation in vivo by administration of exogenous gonadotropins is difficult to manage and costly due to the massive amounts of FSH/LH required for stimulation, and concerns exist over the possibility of increased ovarian cancer in gonadotropin-treated patients. Whittemore et al., *Am. J. Epidemiol.*, 136: 1184–1203 (1992). Another agent of some use is FSH alone or in combination with a gonadotropin releasing hormone antagonist, as described in U.S. Pat. No. 4,845,077.

The treatments with FSH or a mixture of FSH and LH resulted in increased inhibin serum levels during the follicular and early luteal phase of the cycle. McLachlan et al., *Lancet*, 1: 1233–1234 (1986); Tsonis et al., *J. Clin. Endocrinol Metab.*, 66: 915 (1988); Buckler et al., *J. Endocrin.*, 122: 279–285 (1989); Tsuchiya et al., *Fert. Steril.*, 52: 88 (1989). However, another investigator has found that at the time of ovulation neither inhibin activity nor follicular levels of steroid or gonadotropins are adequate criteria for predicting the performance of oocytes in an IVF protocol. Lefevre et al., *Fert. Steril.*, 46: 325 (1986).

Activin A is reported to accelerate germinal vesicle breakdown (GVBD) of immature rat oocytes in vitro. Itoh et al., *Biochem. Biophys. Res. Commun.*, 166: 1479–1484 (1990). Inhibin, on the other hand, reportedly inhibits meiotic maturation of rat oocytes as shown by the suppression of GVBD. O et al., *Mol. Cell. Endo.*, 62: 307–311 (1989).

Routinely in IVF, oocyte collection is timed by the administration of hCG, unless there is an endogenous LH surge. Typically, maturation is completed by culturing the oocytes with their cumulus cells for 4–8 hours. Sathananthan and Trounson, *Gamete Res.*, 5: 191–198 (1982); Trounson et al., *J. Reprod. Fert.*, 64: 285–294 (1982). Various culture media are currently being used for both maturation and fertilization of oocytes. Trounson, in *Clinical in Vitro Fertilization*, Wood and Trounson, eds., 2nd ed. (London: Springer-Verlag, 1989), pp. 32–50. About 40% of oocytes are already at MII at the time of collection. If these MII oocytes age in culture before insemination, the chances of normal fertilization and embryo development of the oocytes are lessened considerably. Postmaturity is also associated with embryo mortality and chromosomal abnormalities. Osborne and Moor, *J, Reprod. Fert.* (Suppl.) 36: 59–72 (1988). oocytes at metaphase I (MI), which have undergone GVBD, are more likely to mature in time for insemination, and oocytes retrieved at the GV stage may still be immature at insemination.

It has been found that GV oocytes will complete meiotic maturation in Ham's F10 medium supplemented with follicular fluid recovered with mature oocytes. Cha et al., *Fertil. Steril.*, 55: 109–113 (1991). These oocytes were fertilized at high rates, cleaved normally, and were capable of development to term (3 of 5 embryos were transferred). While it is thus possible that GV oocytes could be successfully cultured and fertilized to generate pregnancies, and while immature oocytes may undergo spontaneous maturation when released from their ovarian follicles, it would be desirable to enhance the rate and extent of maturation of immature oocytes in vitro so that a higher yield of mature oocytes could be accumulated for ultimate fertilization, such as by IVF. It would also be desirable to improve the quality of the oocytes that are being fertilized to increase the rate of success in fertilization and development.

Moreover, while the ethical advantage of cryopreserving human oocytes rather than embryos is evident, mature oocytes at MII are sensitive to cryoprotectants, cooling, and freezing. Trounson, "Embryo cryopreservation," in *Clinical In Vitro Fertilization*, Wood and Trounson, eds., 2nd ed. (Berlin Springer-Verlag, 1989), pp. 127–142; Trounson and Sathananthan, Human oocyte and embryo freezing, in *Developments in Ultrastructure of Reproduction*, Motta, ed. (New York: Alan R. Liss, 1989), pp. 355–366; Sathananthan et al., *Hum. Reprod.*, 3: 968–977 (1988). Even brief cooling to room temperature from 37° C. irreversibly disrupted spindle microtubules. Pickering et al., *Fertil. Steril.*, 54: 102–108 (1990). Also, it was reported that fertilization of oocytes that were frozen and thawed caused dislocation of some of the chromosomes (Sathananthan and Trounson, "Effect of culture and cryopreservation on human oocyte and embryo ultrastructure and function," in *Ultrastructure of Human Gametogenesis and Early Embryogenesis*, Van Blerkom and Motta, eds. (Boston: Kluwer, 1989), pp. 181–199; Sathananthan et al., *Gamete Res.*, 16: 343–354 [1987]) and polyploidy. Al-Hasani et al., *Hum. Reprod.*, 2: 695–700 (1987). GV murine oocytes have been frozen and then cultured in vitro to maturation (Van Blerkom, *Hum. Repord.*, 4: 883–898 [1989]); however, there is a need for a more efficient method to achieve maturation after cryopreservation.

Accordingly, it is an object of the present invention to increase the rate of maturation of oocytes in vitro before fertilization and embryo transfer.

It is another object to increase the degree of maturation of immature oocytes prior to fertilization and to enhance the quality of oocytes destined for fertilization so as to increase the chances of successful fertilization and subsequent development of a viable embryo.

It is yet another object to utilize what would otherwise be discarded oocytes in the context of an IVF program.

It is still another object to minimize the need for using expensive and time-consuming treatment with gonadotropins and minimize the time necessary for maturation in vitro.

It is a further object to achieve successful fertilization of cryopreserved oocytes, thereby circumventing ethical problems associated with the banking of fertilized human embryos.

It is a still further object to contribute significantly to the fertile oocyte pool required for the propagation of endangered non-human species such as primates or for development of disease models for medical research.

These and other objects will be apparent to one of ordinary skill in the art.

SUMMARY OF THE INVENTION

The present invention provides a method for enhancing the fertility potential of oocytes comprising culturing the oocytes in vitro with an effective amount of inhibin, activin, or a combination of inhibin and activin. The ovaries from which the oocytes are recovered are preferably unstimulated, but also may be stimulated with, for example, elevated levels of endogenous or exogenous gonadotropins.

In a further aspect, the invention provides a method for increasing the rate of maturation of immature oocytes comprising culturing the oocytes in vitro with an effective amount of a combination of inhibin and activin. The invention further provides a culture medium comprising oocytes, activin, and inhibin.

In another aspect, the invention provides a method for fertilizing oocytes comprising removing oocytes from a follicle of an ovary, culturing the oocytes with an effective amount of inhibin, activin, or a combination of inhibin and activin, and mixing the cultured oocytes with spermatozoa, resulting in fertilization.

In a still further aspect, the invention provides a method for storing and then enhancing the fertilization potential of oocytes comprising cryopreserving immature oocytes, thawing the cryopreserved oocytes, and culturing the thawed oocytes in vitro with an effective amount of inhibin, activin, or a combination of inhibin and activin. While cryopreservation can take place by any means, in one aspect the cryopreservation procedure involves cooling oocytes immersed in a cryoprotective solution to a temperature of no more than about $-60°$ C., and storing the cooled oocytes at a temperature of no more than about $-60°$ C.

The ability to culture oocytes in vitro so as to enhance their capability for fertilization and/or to enhance the rate and degree of maturation of immature oocytes could contribute substantially to a gamete pool if the culturing culminated in fertilization and normal embryonic development. The enhancement of the quality of oocytes is expected to play a significant role in human-assisted reproductive technologies (ART) including IVF. Moreover, oocytes from diverse species that would otherwise be wasted can now be employed, such as immature oocytes obtained from primate species at necropsy, immature oocytes obtained during surgical intervention such as oophorohysterectomy, or immature oocytes recovered during hyperstimulation protocols or in natural cycles in the context of an IVF program. Also, oocytes can be removed from cancer patients, such as those with ovarian cancer, prior to chemotherapy, and wedge resection oocytes can be retrieved from gonadotropin-resistant women.

In addition, in vitro culturing of immature oocytes as practiced in accordance with this invention could minimize or even eliminate the need for expensive, time-consuming, and potentially oncogenic gonadotropin stimulation in vivo and may lead to knowledge that will improve IVF outcome. In this respect, increasing the quality of the oocyte without the use of stimulants such as clomiphene citrate and FSH/LH might limit multiple births if fertilization of one good-quality oocyte, rather than multiple irregular oocytes, can be achieved.

Furthermore, since it would be cumbersome or impossible to prepare the gonadotropins FSH and or LH from every endangered species that requires IVF for survival of the species, improvement of ovarian oocyte quality and enhancement in rate and degree of maturation in vitro without FSH/LH follicular and ovarian in vivo stimulation may provide a significant contribution to the fertile oocyte pool required for the propagation of endangered species including non-human primates. It will also be useful for development of disease models for medical research and for increasing the gene pool of genetically manipulated species such as race horses that one wishes to breed.

Additionally, this approach, when combined with cryopreservation of immature or mature oocytes and fertilization in the context of an ART cycle, could circumvent ethical problems associated with the banking of human embryos in that one avoids the freezing of a living being.

Moreover, typically only a low dose (100 ng/ml or less) of reagent is required to achieve effective results, and one oocyte or more can be cultured in 50 µl. Maturation in vitro also has a time advantage in that one day rather than the typical 48–72 hours is required for maturation in vitro.

BRIEF DESCRIPTION OF THE DRAWINGS

FIGS. 4A–4C disclose photographs of the rhesus monkey oocytes after 12–36 hours of culture.

DESCRIPTION OF THE PREFERRED EMBODIMENTS

Definitions:

As used herein, the term "oocytes" refers to the gamete from the follicle of a female animal, whether vertebrate or invertebrate. Preferably, the animal is an endangered species and/or a mammal, and more preferably is a sports, zoo, or other animal whose oocytes would be desirable to save due to superior breeding, such as race horses, an endangered mammalian species, a non-human primate, or a human. "Endangered species" for purposes herein refers to a species of animal that has been deemed to be endangered by the U.S. Endangered Species Act of 1973 or its global counterpart, the World Conservation Union. Typically, the population of an endangered species is threatened due to overhunting, disease, and/or natural habitat destruction so that it can no longer survive in adequate numbers to maintain the species. Examples of endangered species include northern spotted owls, panda bears, highland gorillas, orangutans, chimpanzees, Siberian tigers, elephants, black-crested macaques, golden lion tamarins, etc.

"Immature" oocytes refers to oocytes that are viable but incapable of fertilization without additional growth or maturation. Oocytes recovered from "unstimulated" follicles or ovaries are natural oocytes obtained from follicles or ovaries that were not treated with any gonadotropins or other hormones or agents to stimulate maturation of the oocytes. Oocytes recovered from "stimulated" ovaries may be either mature or immature. Subjective criteria to estimate the viability and maturity of the ovum that can be done microscopically after removal of the ovum from the follicle include assessing the number and density of surrounding granulosa cells, the presence or absence of the germinal vesicle, and the presence or absence of the first polar body.

Oocytes from unstimulated ovaries generally have two or more layers of surrounding condensed granulosa cells, a germinal vesicle, and no polar body, whereas oocytes from stimulated ovaries generally have an expanded granulosa cell layer called the cumulus, no germinal vesicle, and one polar body. Maturity may be measured by the number and density of surrounding granulosa cells, the presence or absence of the first polar body, and the thickness of the zona pellucida, as well as by oocyte resumption of meiotic maturation as expressed by the percentage of GV intact oocytes that undergo GVBD and/or that reach MII after 48 hours of culturing. See also Sathananthan et al., in *Ultrastructure of the Ovary*, supra, for ways to assess nuclear and cytoplasmic maturation of mammalian oocytes.

Figure 3:
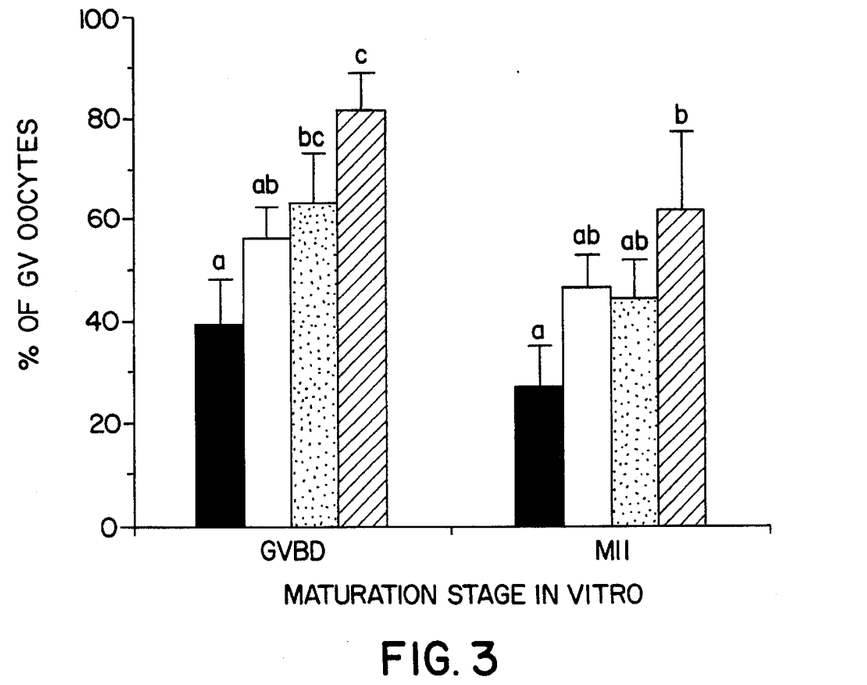
FIG. 3 depicts the effects of various agents on rhesus monkey oocyte maturation in vitro, where oocyte maturation is expressed by the percentage of GV intact oocytes that underwent GVBD or reached MII after 48 hours of culture with the different treatments. The agents tested were those described in the legend to FIG. 1, where solid bars are control, open bars are inhibin, shaded bars are activin, and diagonal bars are the combination of inhibin and activin.

As used herein, the expression "enhancing the fertilization potential of oocytes" refers to increasing the quality of the oocyte so that it will be more capable of being fertilized and producing a viable embryo than would otherwise be the case, and also refers to increasing the extent (degree or percentage) of maturation of immature oocytes, as exemplified by FIG. 3. Maturation is assessed as described above and quality can be assessed by appearance of the oocytes from photographs as exemplified by FIG. 4 and by the IVF rate. Criteria to judge quality of the oocyte by visual means include, for example, their shape, cumulus expansion, GVBD, and extrusion of the first polar body. Immature GV oocytes usually have a compact cumulus and a tight layer of corona cells, while maturing MI oocytes have an expanding cumulus and matured MII oocytes have an expanded cumulus. Also, GV oocytes usually have an eccentric nucleus and no polar body. Maturing oocytes at MI have no nucleus or polar body but do have a spindle. The mature oocytes have a single polar body in the perivitelline space and an MII spindle. In addition, immature or atretic oocytes have a more compact and smooth zona, while mature MII oocytes have a spongy, meshlike appearance. Fertilized ova completing meiosis have two polar bodies in the perivitelline space and two pronuclei in the ooplasm. This latter stage can be measured by using Normarski inverted microscopy or phase microscopy after the cumulus cells are removed by gentle pipetting or dissection.

As used herein, the expression "increasing the maturation rate of immature oocytes" refers to increasing the rate at which maturation of the oocytes occurs over time, whether at the GVBD stage (as in FIG. 1) or MII stage (as in FIG. 2) or both.

"Spermatozoa" refers to male gametes that can be utilized to fertilize the oocytes herein.

As used herein, the term "inhibin" refers to the heterodimers of $\alpha$ and $\beta$ chains of inhibin, prepro forms, and pro forms, together with glycosylation and/or amino acid sequence variants thereof. After cleavage from the mature protein, the precursor portion may be covalently associated with the mature protein. Inhibin A refers to inhibin with the chains $\alpha$ and $\beta_A$. Inhibin B refers to inhibin with the chains of $\alpha$ and $\beta_B$.

As used herein, the term "activin" refers to homo- or heterodimers of $\beta$ chains of inhibin, prepro forms, and pro forms, together with glycosylation and/or amino acid sequence variants thereof. After cleavage from the mature protein, the precursor portion may be covalently associated with the mature protein. Activin A refers to activin with the two chains of $\beta_A$. Activin AB refers to activin with the chains $\beta_A$ and $\beta_B$. Activin B refers to activin with the two chains of $\beta_B$.

Preferably, the inhibin and activin useful herein are human inhibin A or B and human activin A, AB, or B, most preferably human inhibin A and human activin A or human activin B.

The intact isolated prepro or prodomain or mature $\beta_A$, $\beta_B$, and $\alpha$ sequences are suitably synthesized by any means, including synthetic and/or recombinant means, but are preferably synthesized in recombinant cell culture, for example, as described in U.S. Pat. No. 4,798,885, supra.

It is within the scope hereof to employ inhibin and/or activin from animals other than humans, for example, porcine or bovine sources, to treat human oocytes, particularly since inhibin and activin are conserved (90–100% sequence identity) across species. For example, the nucleotide and deduced amino acid sequences of the porcine inhibin $\alpha$ chain are found in U.S. Pat. No. 4,798,885, supra, and of the porcine activin $\beta$ chain are found in FIGS. 2A and 2B of U.S. Pat. No. 4,798,885, supra. Likewise, if it is desirable to treat the oocytes from other species such as endangered or domestic and farm animals and zoo, sports or pet animals, human inhibin and/or activin, as well as inhibin and/or activin from other species, is suitably employed.

Generally, amino acid sequence variants will be substantially homologous with the relevant portion of the mammalian $\alpha$ and $\beta$ chain sequences set forth in, e.g., U.S. Pat. No. 4,798,885, supra. "Substantially homologous" means that greater than about 60% of the primary amino acid sequence of the homologous polypeptide corresponds to the sequence of the inhibin or activin chain when aligned to maximize the number of amino acid residue matches between the two proteins. Alignment to maximize matches of residues includes shifting the amino and/or carboxyl terminus, introducing gaps as required, and/or deleting residues present as inserts in the candidate. Typically, amino acid sequence variants will be greater than about 70% homologous with the corresponding native sequences.

While the site for introducing a sequence variation is predetermined, it is unnecessary that the mutation per se be predetermined. For example, to optimize the performance of a mutation at a given site, random mutagenesis may be conducted at the target codon or region and the expressed inhibin or activin mutants screened for the optimal combination of desired activity. Techniques for making substitution mutations at predetermined sites in DNA having a known sequence are well known, for example, M13 primer mutagenesis.

Mutagenesis is conducted by making amino acid insertions, usually on the order of about from 1 to 10 amino acid residues, or deletions of about from 1 to 30 residues. Substitutions, deletions, insertions, or any subcombination may be combined to arrive at a final construct. Preferably, however, substitution mutagenesis is conducted. Obviously, the mutations in the encoding DNA must not place the sequence out of reading frame and preferably will not create complementary regions that could produce secondary mRNA structure.

Covalent modifications of inhibin and activin are included within the scope of the invention, and include covalent or aggregative conjugates with other chemical moieties. Covalent derivatives are prepared by linkage of functionalities to groups that are found in the inhibin or activin amino acid side chains or at the N- or C-termini, by means known in the art. For example, these derivatives will include: aliphatic esters or amides of the carboxyl terminus or residues containing carboxyl side chains, e.g., aspartyl residues; O-acyl derivatives of hydroxyl group-containing residues such as aryl or alanyl; and N-acyl derivatives of the amino terminal amino acid or amino-group containing residues, e.g., lysine or arginine. The acyl group is selected from the group of alkyl moieties (including C3 to C10 normal alkyl), thereby forming alkanoyl species, and carbocyclic or heterocyclic compounds, thereby forming aroyl species. The reactive groups preferably are difunctional compounds known per se for use in crosslinking proteins to insoluble matrices through reactive side groups, e.g., m-maleimidobenzoyl-N-hydroxy succinimide ester. Preferred derivatization sites are at histidine residues.

Modes for Carrying Out the Invention:

The present invention concerns itself with using inhibin or activin, or a combination of inhibin with activin, to enhance the fertility potential of animal oocytes, especially those of mammals, including sports, zoo, pet, and farm animals such as dogs, cats, cattle, pigs, horses, monkeys, and sheep, endangered species, and humans. Further, the present invention relates to using a combination of inhibin and activin to increase the rate of maturation of the oocytes, which combination is found to work better than either agent alone.

The methods of this invention involve first removing the oocytes, preferably immature oocytes, from follicles in the ovary. This is suitably accomplished by conventional techniques, for example, using the natural cycle as described below, using anovulatory methods, during surgical intervention such as oophorohysterectomy, during hyperstimulation protocols in the context of an IVF program, or by necropsy. In the natural cycle, when the schedule of ovarian events progresses as expected, a burgeoning follicle(s) on the ovarian surface can be viewed near midcycle by ultrasound or laparoscopy, having distended vessels and substantial translucence. This is the familiar appearance of the dominant follicle near ovulation. A needle is passed into the follicle and its contents, which may be a single oocyte, are aspirated. Oocyte removal and recovery is suitably performed by means of transvaginal ultrasonically guided follicular aspiration. Following evacuation, the follicle collapses. After the follicle is aspirated, the ovum is recovered and examined microscopically to assess its condition. Additional smaller follicles may be aspirated in turn. Subjective criteria to estimate the normality of the ovum include assessing its maturity by the number and density of surrounding granulosa cells, the presence or absence of the first polar body, and the thickness of the zona pellucida, as well as other criteria mentioned above.

However, as stated above, the invention is not limited to use of immature oocytes. Thus, suitable oocytes include those that are from ovaries stimulated by administration to the oocyte donor of a fertility agent or fertility agent enhancer, so that the oocytes are in a greater state of maturity than oocytes from unstimulated ovaries. Examples of agents used to induce such controlled multiple follicular maturation include inhibin administered directly to the ovary (WO 91/10445, supra), clomiphene citrate or human menopausal gonadotropins, e.g., FSH as described in U.S. Pat. 4,845,077, or a mixture of FSH and LH, and/or human chorionic gonadotropins.

A gonadotropin releasing hormone antagonist may be administered to decrease the marked individual variability in response to human menopausal gonadotropin therapy. Typical gonadotropin hormone releasing antagonists are described by Rees et al., *J. Med. Chem.*, 17: 1016 (1974); coy et al., *Peptides,* 1976 (Loffed Ed., Editions de L'Universite de Bruxelle 1977) p. 463, Beattie et al., *J. Med. Chem.*, 18: 1247 (1975); Channabasavaiah et al., *Biochem. Biophys. Res. Commun.*, 86: 1266 (1979); and U.S. Pat. Nos. 4,317,815 and 4,431,635. These include (Ac-pClPhe$^1$, pClPhe$^2$, DTrp$^3$, DArg$^6$, DAla$^{10}$)GnRH HCl, [D-Phe$^2$]-LHRH, [D-Phe$^2$, D-Phe$^6$]-LHRH, [D-Phe$^2$, Phe$^3$, D-Phe$^6$]-LHRH, [D-Phe$^2$, D-Trp$^3$, D-Phe$^6$]-LHRH, [D-p-F-Phe-D-Ala$^6$]-LHRH, and [Ac-D-Phe$^1$, D-Phe$^2$, D-Trp$^{3,6}$]-LHRH.

These fertility agents are used in the amounts typically employed for such agents. For example, if FSH is used, preferably the effective amount given to the female before the oocytes are collected is a daily amount of about 70 to 220 I.U./kg, more preferably 1.5 to 4.0 I.U./kg. If a gonadotropin releasing hormone antagonist is used in conjunction with FSH, preferably the daily amount of gonadotropin releasing hormone antagonist is about 1.0 to 4.0 mg/kg, more preferably 1.5 to 2.5 mg/kg. Further details on administration of these latter agents can be found in U.S. Pat. No. 4,845,077.

Once the desired oocytes have been isolated (e.g., viable oocytes selected from microscopic examination), they are suitably cultured in accordance with this invention or cryopreserved for storage in a gamete or cell bank for future culturing. If they are not to be frozen first, the oocytes should be cultured no more than about 48 hours after aspiration from the follicle or until the first polar body is released. If they are frozen, when it is desired to use them, they are thawed and then cultured by the invention method described herein.

Development of a cryoprotective methodology requires optimization of each individual component in the process through independent study followed by an integrated approach, combining optimal components, to identify the final process. Optimal freezing, storing, thawing, and rinsing procedures that are compatible with maintaining maximal viability are identified. Any method for freezing the oocytes can be utilized. For example, an ultrarapid freezing technique can be employed, as described in Trounson et al., *Fertil. Steril.*, 48: 843–850 (1987) and Vasuthevan et al., *Fertil. Steril.*, 58: 1250–1253 (1992). Specific protocols for cryopreserving epithelial sheets and blood vessels that may be useful in the present invention are described in U.S. Pat. Nos. 5,145,770 and 5,145,769, respectively, the disclosures of which are incorporated herein by reference. One detailed method for cryopreservation of oocytes is set forth below, where modifications can be made as necessary to suit the individual treatment.

First, the oocytes are equilibrated in a cryopreservative solution for a time sufficient to allow the cryopreservative to mix thoroughly with and/or displace the water within and between the oocytes. Second, the oocytes are cooled to at least about −60° C., preferably to about −180° C. to −196° C., at a rate slow enough for the cryoprotected cells to avoid intraCellular ice crystal formation and subsequent damage. The frozen oocytes may be stored for long periods at about −180° C. or for shorter periods at higher temperatures, e.g., as high as about −60°–65° C. Third, before use, the oocytes are warmed at room temperature in air or other gas, and then thawed completely by rapid warming in, for example, a water bath. Fourth, the cryoprotectant is removed from the oocytes by rinsing in an isotonic buffer such as lactated Ringer's solution, or in the culture medium to be used for enhancing the fertilization potential of the oocytes.

Standard cryoprotective medium is composed of a physiologically balanced salt solution (e.g., cell culture medium) supplemented with bovine serum and a cryoprotectant such as glycerol, propanediol, or dimethylsulfoxide, cell-penetrating, glass-forming agents. These cryoprotectants have been used successfully for cryopreserving cells in suspension, including fertilized embryos. In addition, non-cell-penetrating, glass-forming agents may be added as described in U.S. Pat. No. 5,145,770, supra, as well as the cryopreservative mentioned in U.S. Pat. No. 5,145,769, supra.

The cryopreservation process in general requires immersing the oocytes to be frozen in cryoprotective medium for a time sufficient to permit equilibration of the cells with cryoprotectant. Generally, the equilibration time is for up to about two hours or more in cryoprotectant prior to freezing without affecting the viability of the Cells. The equilibration is conducted more typically for about 20–30 minutes, at about 17° C. to about 30° C., typically at room temperature, in a cryoprotective solution, in a shallow storage dish.

Following equilibration, the oocytes and the cryoprotectant solution are transferred to a straw or vial that is sealed so that it is gas and water-tight. The oocytes in the sealed container are cooled to at least about −60° C. (e.g., with dry ice), preferably below −120° C., and to promote longer-term storage, to approximately −180° C. to about −196° C. The cooling rate preferably is slow (e.g., no more than about 1° C./min.) from about 0° C. to at least −30° C. This serves to discourage ice crystal formation. Preferably, cooling is conducted at the outset in a rate-controlled cooling device such as a commercial programmable cell freezer (Cryomed, Inc. No. 1010/2700) to a temperature of about −30° C. to −100° C., preferably about −80° C. to −85° C., and then the contents are transferred to a liquid nitrogen storage vessel and maintained in vapors of liquid nitrogen to reduce its temperature further.

The preferred freezing protocol cools the oocytes in the sealed container until the oocytes are approximately 4° C. Then the oocytes are cooled at about 1° C. per minute to about −6° or −7° C. and the solution is seeded. After an equilibration period of about 10 minutes, the mixture is cooled at about 0.3° C. per minute. Once the temperature of the oocytes reaches at least about −30° C., and preferably at least about −85° C., the container is transferred to a liquid nitrogen refrigerator and stored at about −180° C. (nitrogen vapors) or about −196° C. (liquid nitrogen).

Thawing the oocytes is suitably accomplished by removing the sealed container from the liquid nitrogen refrigerator and preferably keeping it at room temperature in air for about 1 minute and up to about 3 to 5 minutes. This produces a warming rate of between about 20° C./min. and about 100° C./min. The oocytes may then be heated to room temperature without regard to the rate of heating. Preferably the last stage is conducted by submerging the sealed container in a water bath until the oocytes are thawed. This prevents the zonae pellucidae surrounding frozen oocytes from cracking. Alternatively, the water bath is eliminated and the oocytes are thawed at room temperature; however, this takes longer than the water bath and often has the effect of reducing cell viability.

Once the oocytes are thawed, the container is suitably opened and the cryopreservative solution replaced by an isotonic buffer solution at physiological pH (about 6.8 to 7.4), preferably FAD medium or lactated Ringer's solution or the culture medium to be used to enhance the fertilization potential of the oocytes, to dilute out the cryoprotectant. Not all isotonic buffered solutions at physiological pH may be acceptable for dilution of cryoprotectant. Phosphate buffered saline and standard saline may reduce viability significantly. The thawed oocytes are equilibrated preferably at about room temperature in rinsing buffer or culture medium preferably for about 15 minutes and may remain there for up to about 4 hours. Direct microscopic visualization can be used to determine if the oocytes are still viable as compared to non-frozen, non-stored control oocytes.

After placement in the rinsing solution for a sufficient period of time, the oocytes can then be cultured as described herein.

Alternatively, after removal from the follicle the oocytes are cultured and then frozen before fertilization is carried out, as described below. The culturing takes place in a suitable culture medium that includes at least inhibin, activin, or a combination of inhibin and activin in an amount effective to enhance the fertility potential of oocytes in general, and to enhance the rate and the extent of maturation of immature oocytes and the quality of the oocytes in particular. The culture medium herein is generally one containing physiologically balanced salts, energy sources, and antibiotics and is suitable for the species whose oocytes are being treated. Examples of suitable media for certain species such as humans and monkeys include human tubal fluid (HTF), as obtained from Quinn et al., *Fertil. Steril.*, 44: 493 (1985), supplemented with 10% heat-inactivated maternal or fetal cord serum, which is typically used for IVF and embryo culture, TALP, as obtained from Boatman, in *In Vitro Growth of Non-Human Primate Pre- and peri-implantation Embryos,* ed. Bavister, pp. 273–308 (New York: Plenum Press, 1987), Ham's F-10 medium, Menezo's $B_2$ medium (BioMerieux SA, France), Earles medium (Sigma Chemical Co., St. Louis, Mo.), etc. General reviews describing these types of media include Menezo and Khatchadourian, "The Laboratory Culture Media," *Assisted Reproduction Reviews,* 1: 136 (1991) and Leese, "Metabolism of the Preimplantation Mammalian Embryo," *Oxford Reviews of Reproductive Biology,* 13: 35–72 (1991), ed. S. R. Milligan, Oxford University Press. The practitioner will be able to devise the necessary medium suitable for the species. The pH of the culture medium is generally about 7 to 8, more preferably about 7.2–7.6.

The conditions required for culturing the oocytes depend on, for example, the type and number of oocytes being treated. Typically the culturing temperature is in the range of about 36°–39° C., although temperatures outside this range may also be suitable, for example, about 35°–40° C. The culturing time is at least about 1 hour, preferably about 4 to 100 hours, and more preferably about 12 to 36 hours. Typically the culturing environment contains about 95–100% humidity, 5% $CO_2$, 5% $O_2$, and 90% $N_2$. Vessels of tissue-culture-grade plastic useful for carrying out the culturing include test tubes, vials, organ-culture dishes, petri dishes, or microtiter test plates.

The effective amount of inhibin and/or activin contained in the culture medium will take into account, for example, whether inhibin or activin alone is used or whether the combination is used, the species from which the oocyte was removed, the number of oocytes being treated, the toxicity or undesirable effects of using an excess of the inhibin and/or activin, and other factors known to practitioners.

As a general proposition, the total pharmaceutically effective amount of each of inhibin or activin in the culture medium will be at least about 0.01 ng/ml of culture medium, more preferably at least about 0.1 ng/ml, more preferably still in the range of about 1 ng/ml to about 100 mg/ml of culture medium, more preferably yet from about 10–100 ng/ml to about 10 mg/ml of culture medium, although, as noted above, this will be subject to a great deal of therapeutic discretion. The key factor in selecting an appropriate dose is the result obtained, e.g., enhancement in the rate and/or extent of oocyte maturation or enhancement in quality of the oocytes, each of which can be assessed by the criteria provide above, or by other criteria as deemed appropriate by the practitioner. If a combination of inhibin and activin is employed, amounts of each agent can be somewhat less than those amounts given above, and this will be within the discretion and skill of the medical practitioner.

For treatment of the oocytes the inhibin or activin alone or the combination of inhibin and activin are formulated generally by mixing them separately or together at the desired degree of purity, in a form such as a solution, suspension, or emulsion, with a pharmaceutically acceptable carrier, i.e., one that is not toxic to the oocytes at the dosages and concentrations employed and is compatible with other ingredients of the culture medium. For example, the carrier for the inhibin and/or activin preferably does not include oxidizing agents and other compounds that are known to be deleterious to polypeptides.

If a combination is used, the inhibin and activin are suitably added to the culture medium by separate or the same means. In general, the inhibin and/or activin are present before the oocytes are added.

Once the oocytes are matured or stimulated to the point of being capable of fertilization, as indicated by any one or more of the factors noted above or others, they are mixed with suitable spermatozoa from the same species, resulting in fertilization. The fertilization with sperm can be carried out in vitro by known techniques including sperm injection or in vivo, including those indicated below and newer technologies for effecting fertilization.

Examples of human in vitro fertilization and embryo transfer procedures that may be successfully carried out using the method of this invention include, e.g., in vitro fertilization and embryo transfer (IVF-ET) (Quigly et al., *Fertil. Steril.* 38: 678 [1982]), gamete intrafallopian transfer (GIFT) (Molloy et al., *Fertil. Steril*, 47: 289 [1987]), and pronuclear stage tubal transfer (PROST). Yovich et al., *Fertil. Steril*, 48: 851 (1987). Successful such procedures are positively correlated with the number of oocytes retrieved and the number of viable embryos transferred.

In IVF-ET, the oocytes are inseminated with washed and migrated spermatozoa (typically 100,000 to 200,000 per oocyte). Fertilization is assessed typically 12 to 18 hours after insemination and the oocytes are transferred to growth media such as HTF, Ham's F-10, or Earles. Only normal embryos are transferred to the patients at the 2- to 8-cell stage at typically 48 to 56 hours after retrieval.

General protocols for IVF include those disclosed by Trounson et al., supra; Trounson and Leeton, in Edwards and Purdy, eds., *Human Conception in Vitro* (New York: Academic Press, 1982), and Trounson, in Crosignani and Rubin, eds., *In Vitro Fertilization and Embryo Transfer*, p. 315 (New York: Academic Press, 1983), the disclosures of all of which are incorporated herein by reference.

The threat of non-hormone-induced luteal phase hormonal deficiency that may occur in IVF may be ameliorated by administration of progesterone.

For the PROST protocol, all procedures for oocyte aspiration, enhancement of fertilization potential, semen suspension preparation, and insemination are performed using the same procedure as in the IVF program. After the assessment of oocyte fertilization, pronuclear oocytes are transferred into the fallopian tube by the same procedure as in the GIFT program, wherein the fallopian tube is catheterized as described by Molloy et al., *Fert, Steril.*, 47: 289 (1987).

Another method and apparatus for IVF is found in WO 92/20359 published 26 Nov. 1992, wherein the oocytes to be fertilized are placed in individual, low-volume oocyte chambers disposed about the periphery of a microdrop of fertilization medium. A sperm sample, particularly an unfractionated sperm sample, is then placed in the center of the microdrop. Motile sperm tend to move rapidly toward the periphery of the microdrop, resulting in an in situ separation of motile from non-motile sperm. Once at the periphery, fertilization by sperm that enter the oocyte chambers is facile because of the low volume of the chamber.

The invention will be more fully understood by reference to the following examples. They should not, however, be construed as limiting the scope of the invention. All literature and patent citations are expressly incorporated by reference.

EXAMPLE 1

The purpose of this example was to investigate the effect of inhibin, activin, and a combination of inhibin and activin on rhesus monkey oocyte maturation in vitro and on the quality of the oocytes thus treated.

Immature oocytes were recovered from excised ovaries of four regularly cycling female rhesus monkeys (5–13 years of age) from the Oregon Regional Primate Research Center in Beaverton, Oreg. Monkeys were subjected to oophorectomy (surgical removal of ovaries). Ovaries were recovered from anaesthetized animals by paramedian pelvic laparotomy. Preoperatively, monkeys received atropine (0.3 mg, intramuscularly, Eli Lilly, Indianapolis, Ind.) and succinylcholine chloride (20 mg, intravenously, Quelicine™ brand from Abbott Labs, Chicago, Ill.), immediately followed by intubation and anesthesia with 1.0 to 1.5% halothane (Halocarbon Labs, Hackensack, N.J.) vaporized with $N_2O:O_2$ (1:4). The ovaries were collected in TALP culture medium containing HEPES (4-[2-hydroxyethyl]-1-piperazineethanesulfonic acid) culture medium with heparin (25 IU/ml), pH 7.4 at 37° C. TALP culture medium and TALP-HEPES were made fresh using the technique described by Boatman, in *In Vitro Growth of Non-Human Primate Pre- and Peri-implantation Embryos*, supra). Both TALP and TALP-HEPES were at pH 7.4 and at an osmolality of 285–295 mOsm.

Within 10 minutes of oophorectomy, under a dissecting microscope, the ovaries were sectioned in quarters. Ovaries from each female formed a replicate. All manipulations were done in TALP-HEPES at 37° C. Antral follicles were individually excised and punctured with a 25-gauge needle. The released oocytes were collected and pooled at intervals into 500-µl drops of TALP-HEPES under 6 ml of TALP-equilibrated, sterile mineral oil (Sigma, St. Louis, Mo.) at 37° C. At the time of collection, the oocytes were measured using an ocular micrometer. Oocytes smaller than 100 μm in vitelline diameter, with less than two layers of condensed granulosa cells, or oocytes that were obviously degenerate (vacuolated cytoplasm, cytolysis, necrosis, or loss of spherical shape) were excluded from this study.

Within 60 minutes of collection, the oocyte-cumulus complexes (OCC) were assigned randomly to one of four in vitro culture conditions: TALP culture medium alone obtained as described above (control) or TALP medium containing 100 ng/ml of recombinant human inhibin A, 100 ng/ml of recombinant human activin A, or 100 ng/ml of each of recombinant human inhibin A and recombinant human activin A. The recombinant forms of human activin A and human inhibin A employed herein are described in U.S. Pat. No. 4,798,885, supra. They are also available from Genentech, Inc., South San Francisco, Calif. as pre-clinical research reagents. Both reagents are produced as sterile, endotoxin-free reagents.

OCCs were placed individually in 50-μl drops of one of the above four cultures in a culture dish under 5 ml of TALP-equilibrated, sterile mineral oil and incubated in a humidified atmosphere of 5% $CO_2$ in air at 37° C. The OCCs were examined and evaluated periodically on a Nikon Diaphot-TMD™ inverted microscope using Hoffman™ optics at 400× at 6, 12, 24, 30, 36, and 48 hours after culture. Parameters evaluated were: cumulus expansion and mucification, GV presence or absence (GVBD), and polar body presence or absence. The absence of a GV and the presence of a polar body were the measures of complete nuclear maturation (MII). After 24 hours of culture, cumulus cells were dispersed from the oocytes by gentle pipetting through appropriately sized hand-pulled glass pipettes.

Figure 1:
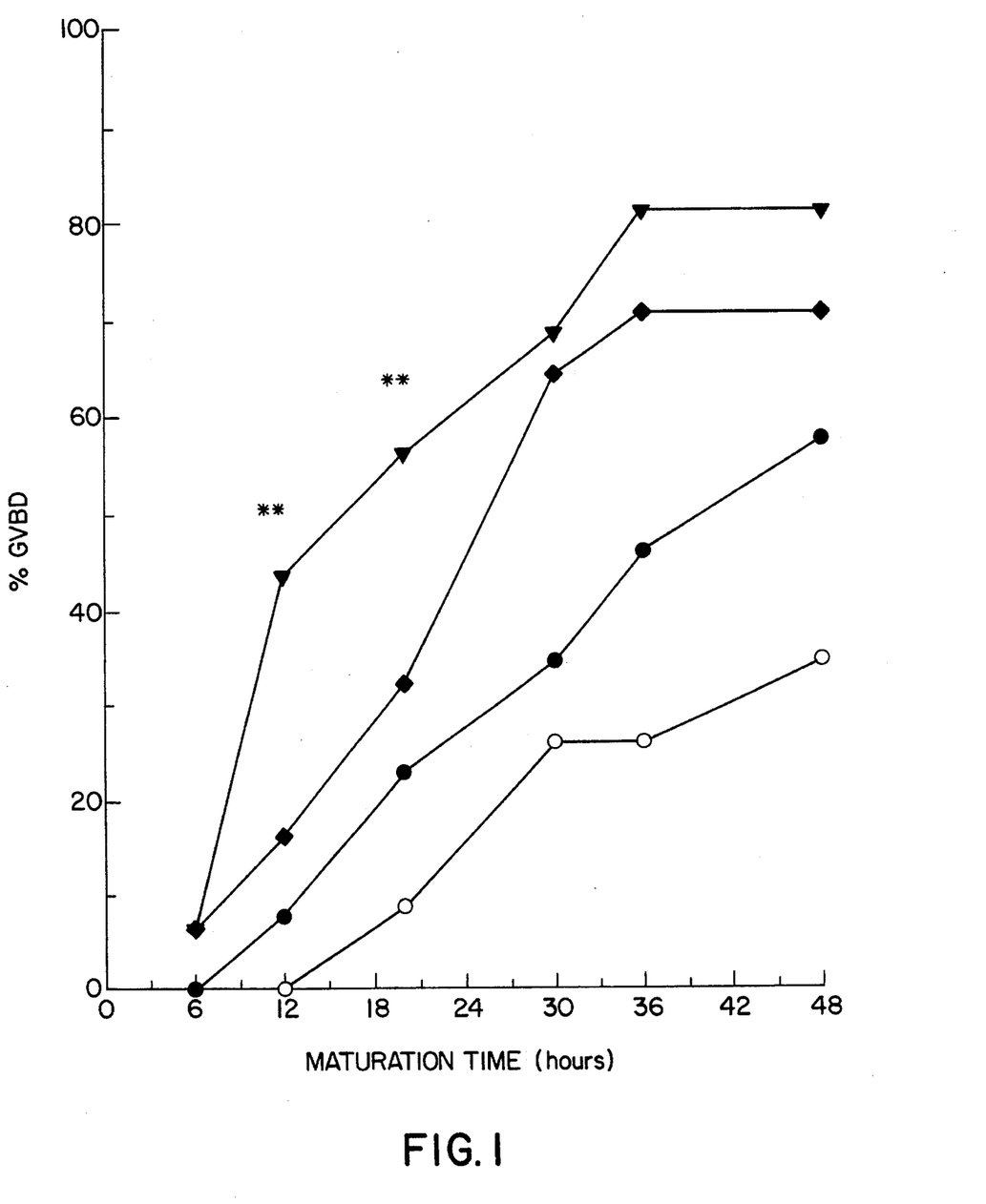
FIG. 1 summarizes the effects of various agents on the time course of rhesus monkey oocyte maturation in vitro, where oocyte resumption of meiotic maturation is expressed by the percentage of GV intact oocytes that underwent GVBD with each treatment. The agents tested were placebo control (23 GV oocytes examined, open circles), inhibin (26 GV oocytes examined, solid circles), activin (32 GV oocytes examined, diamonds), and the combination of inhibin and activin (16 GV oocytes examined, triangles). $*=p<0.05$, and $**=p<0.01$.
Figure 2:
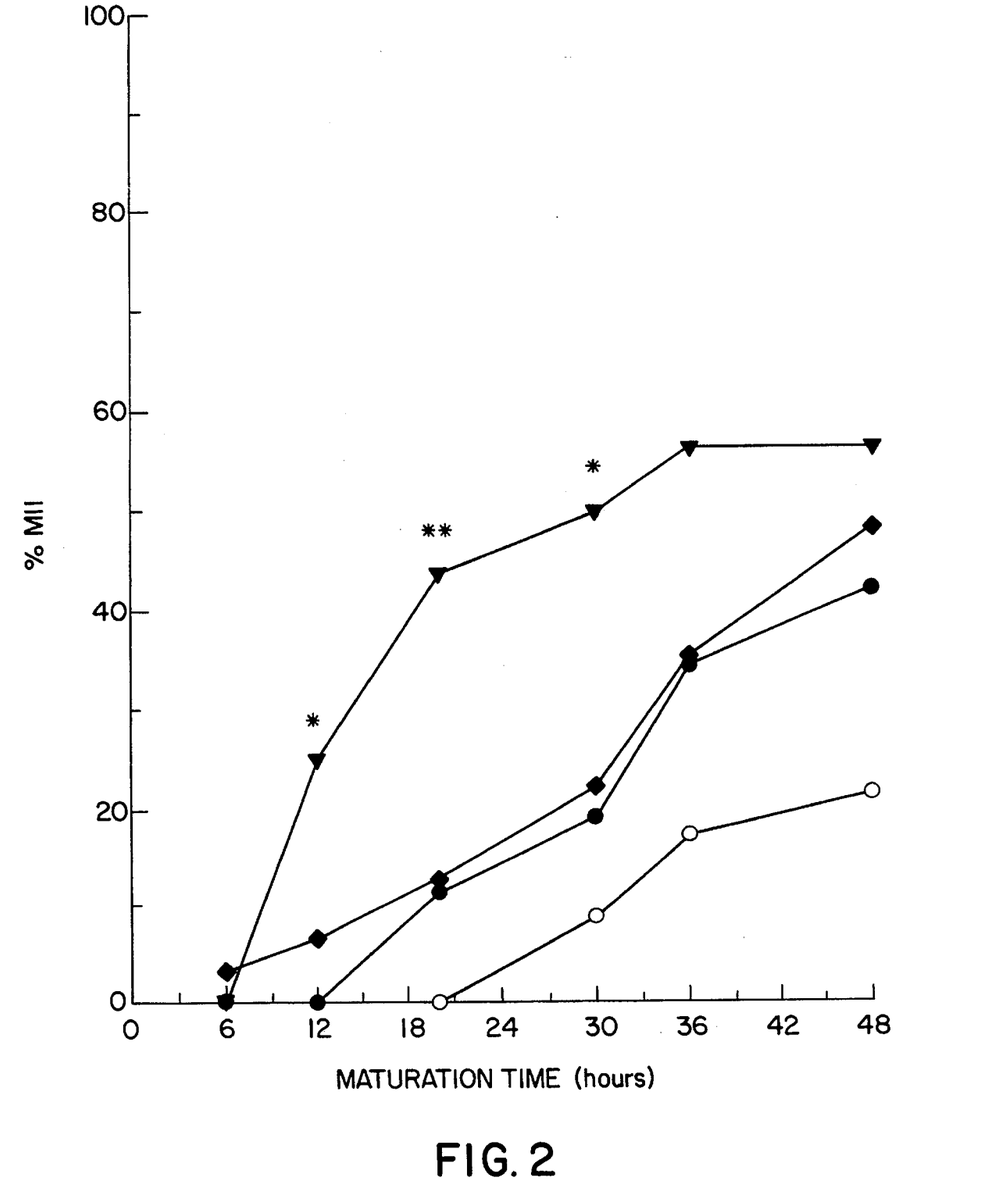
FIG. 2 shows the effects of various agents on the time course of rhesus monkey oocyte maturation in vitro, where oocyte resumption of meiotic maturation is expressed by the percentage of GV intact oocytes that reached MII with each treatment. The agents tested and p values are those described in the legend to FIG. 1.

Data for FIGS. 1–3 were from four experiments. In FIG. 3 data are expressed as the mean percentage ± SE and different superscripts (a, ab, bc, c, and b) vary significantly $p<0.05$ within stage. Data for FIG. 4 were from three experiments and were expressed as the mean percentage ± SE. Statistical analyses for FIGS. 1 and 2 were done using Fisher's exact test, and for FIGS. 3 and 4 were done using one-way analysis of variance (ANOVA) for repeated measures.

FIG. 1 indicates that the enhancement in the rate of rhesus monkey oocyte maturation with inhibin or activin alone was not statistically significant, as indicated by GVBD after 12 and 20 hours of incubation. However, incubation with the inhibin-activin combination significantly accelerated oocyte maturation (i.e., increased the maturation rate) over the control values by 44% and 48% ($p<0.01$) after 12 hours and 20 hours of incubation, respectively.

FIG. 2 indicates that the inhibin-activin combination significantly enhanced the rate of oocyte meiotic maturation to the MII stage, as indicated by extrusion of the first polar body. At 12, 20, or 30 hours of incubation, the inhibin-activin combination elevated oocyte maturation to MII over the control values by 25%, 43%, and 50%, respectively ($p<0.05$). This enhancement in the rate of maturation to MII was not observed with either inhibin or activin alone.

FIG. 3 indicates that 36 or 48 hours of incubation with inhibin alone, with activin alone, and with the inhibin-activin combination all significantly increased the extent of maturation of the oocytes. Thus, the percentage of rhesus monkey oocytes that underwent GVBD from 39.3% for the control group to 57%, 63%, and 82%, respectively ($p<0.01$). Also, significant increases in the percentage of oocytes that matured to MII were observed using inhibin or activin alone as compared to control oocytes, and more than a two-fold increase in the percentage of immature oocytes that reached MII was observed in the presence of the inhibin-activin combination over control oocytes (62.2% vs. 27.4%, respectively).

Figure 4A:
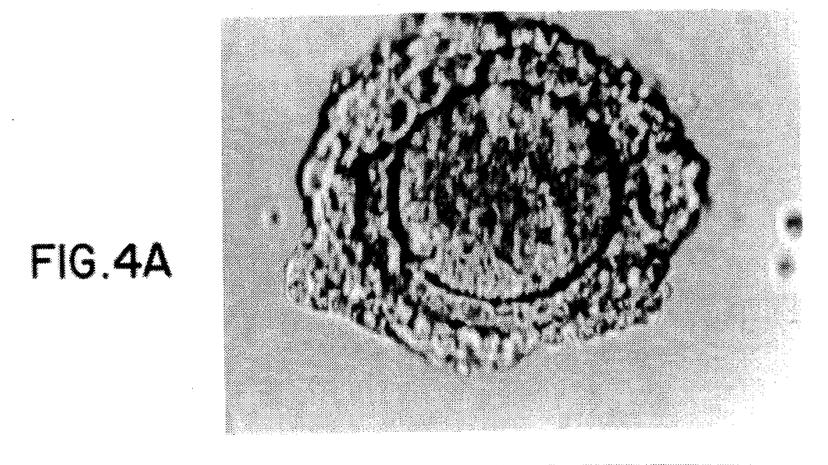
FIG. 4A is a photograph of a control (untreated) oocyte after 24 hours of culture.
Figure 4B:
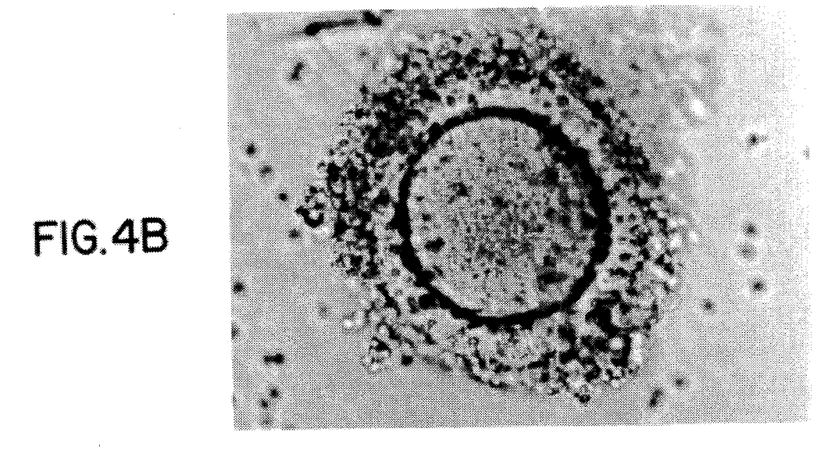
FIG. 4B is a photograph of a GVBD oocyte 12 hours after culture in the presence of the combination of inhibin and activin.
Figure 4C:
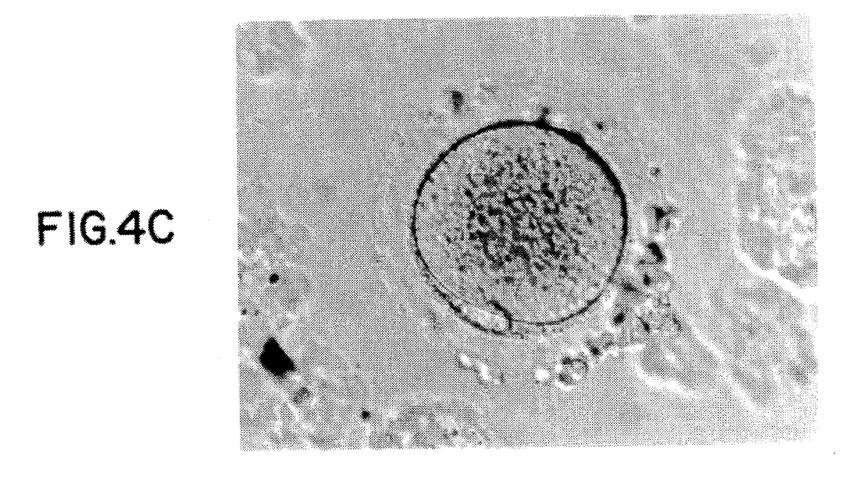
FIG. 4C is a photograph of a MII oocyte 36 hours after culture in the presence of activin alone.

FIG. 4 shows photographs (400×, Hoffman™ optics) of the control oocytes cultured for 24 hours (FIG. 4A) as well as the oocytes cultured as described above using the combination of inhibin and activin for 12 hours (FIG. 4B) and using activin alone for 36 hours (FIG. 4C). The quality of the oocytes was subjectively assessed by such criteria as shape of the oocytes, cumulus expansion, GVBD, and extrusion of the first polar body.

It can be seen from the photographs that in the control oocyte the germinal vesicle was still intact and the granulosa cells were densely attached to the oocyte. The oocyte treated with the inhibin-activin combination for 12 hours underwent GVBD, and the cumulus cells expanded. The oocyte treated with activin alone for 36 hours showed a distinct perivitelline space and a first polar body. Thus, it is clear from the appearance of the oocytes in the photographs that the quality of the oocytes treated with activin and the combination is significantly better than that of the control oocytes. The quality of the oocytes treated with inhibin alone is the same as that of the oocytes treated with activin or the combination after a comparable period of culturing.

EXAMPLE 2

Human follistatin (FS), which bioneutralizes both inhibin and activin, was used in a series of experiments to evaluate whether the effects of activin and the inhibin-activin combination on the rate and degree of in vitro maturation of primate oocytes was specific.

As described in Example 1, immature oocytes recovered from excised ovaries of regularly cycling rhesus monkeys (N=3) were cultured in vitro in either a TALP culture medium alone (control) or in the presence of 100 ng/ml of activin, 100 ng/ml each of inhibin and activin, 100 ng/ml of FS, 100 ng/ml each of activin and FS, or 100 ng/ml each of inhibin, activin, and FS. The purified recombinant human FS employed in this Example was obtained by standard methods of recombinant expression as described by Esch et al., *Mol. Endocrinol.*, 1: 849–855 [(1987) and Shimasaki et al., *Proc. Natl. Acad. Sci. USA*, 85: 4218–4222 (1988).

Figure 5:
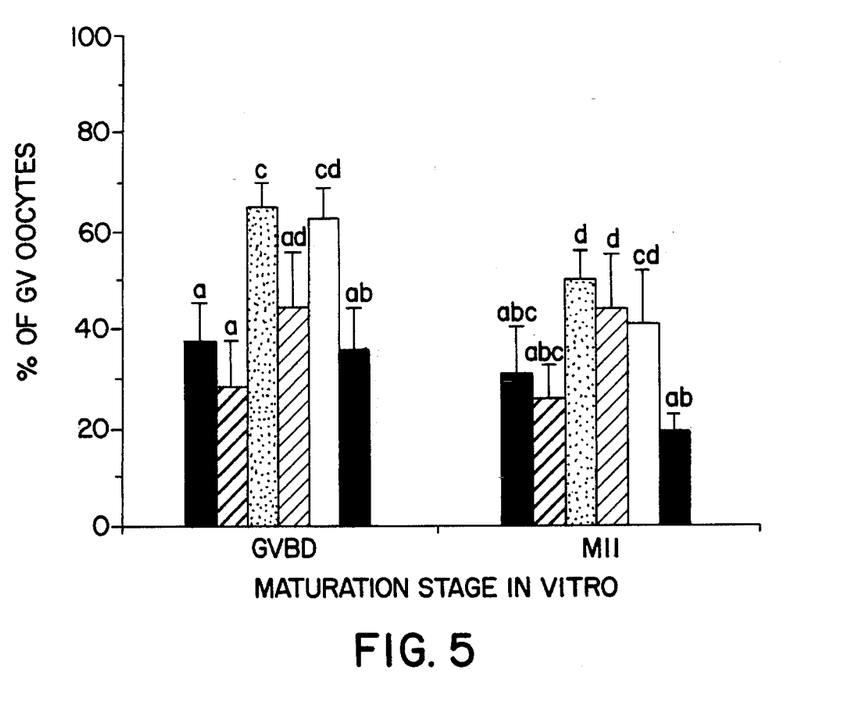
FIG. 5 shows the effects of follistatin (FS) on the maturation of rhesus monkey oocytes, wherein oocyte maturation is expressed by the percentage of GV oocytes that underwent GVBD or reached MII after 48 hours of culture with the different treatments. The treatments were control (26 GV oocytes examined, solid bar to left), FS (24 GV oocytes examined, dark diagonal bars), activin (14 GV oocytes examined, shaded bars), activin plus FS (18 GV oocytes examined, light diagonal bars), inhibin plus activin (22 GV oocytes examined, open bars), and inhibin plus activin plus FS (17 GV oocytes examined, solid bars to right).

The results, provided in FIG. 5, where different superscripts (a, c, ad, cd, ab, abc, and d) vary significantly (p <0.05) within stage, showed that FS negated the enhancing effect of activin and of the inhibin-activin combination ($p<0.05$) on the rate and degree of oocyte maturation. When added to culture medium that contained activin or the inhibin-activin combination FS lowered the percentage of immature oocytes that underwent GVBD to a level similar to that of the FS group or the control group (37.4%, 28.5%, 65%, 44.4%, 62.9%, and 35.8% for the control, FS alone, activin alone, activin + FS, inhibin + activin, and inhibin + activin + FS groups, respectively).

EXAMPLE 3

Immature oocytes were cultured with inhibin, activin, or a combination of inhibin and activin as described in Example 1. The cultured oocytes reaching MII stage were then challenged with sperm from rhesus monkeys and fertilized in vitro using standard techniques known in the art. The fertilization rate of MII oocytes treated with inhibin (51%), activin (45%), and the combination of inhibin and activin (68%) was increased over that of the control (untreated) oocytes (23%). These results show that the improved quality of the treated oocytes translated into an increase in fertilization rate for the treated oocytes.

This invention demonstrates for the first time that inhibin, activin, and the combination of inhibin and activin are potent stimulators of oocyte meiotic resumption from both a qualitative and a quantitative perspective. These agents substantially increase the extent of maturation and the quality of the oocytes in general, thereby increasing fertilization capability. Further, the use of the combination substantially enhances the rate of maturation of immature oocytes in vitro.

What is claimed is:

1. A method for increasing the number of mature primate oocytes, comprising:
   culturing in vitro immature primate oocytes in a culture medium comprising human inhibin and human activin; wherein said human inhibin and said human activin are both present in an amount effective to increase the number of mature primate oocytes.

2. The method of claim 1, wherein said immature primate oocytes are removed from unstimulated ovaries.

3. The method of claim 1, wherein said primate is a human.

4. The method of claim 1, further comprising mixing the cultured oocytes with spermatozoa, thereby resulting in fertilization.

5. The method of claim 4, wherein said fertilization takes place in vitro.

6. The method of claim 4, wherein said fertilization takes place in vivo.

7. The method of claim 1, wherein the effective amount of said human inhibin is at least about 0.01 ng/ml of culture medium and the effective amount of said human activin is at least about 0.01 ng/ml of culture medium.

8. The method of claim 1, further comprising cryopreserving the cultured oocytes.

9. The method of claim 8, further comprising thawing the cryopreserved oocytes to produce intact, viable oocytes capable of fertilization.

10. The method of claim 9, further comprising fertilizing the thawed oocytes.

11. A method for increasing the rate of maturation of immature primate oocytes, comprising:
    culturing in vitro immature primate oocytes in a culture medium comprising human inhibin and human activin; wherein said human inhibin and said human activin are both present in an amount effective to increase the rate of maturation of said immature primate oocytes.

12. A method for fertilizing primate oocytes, comprising:
    removing immature primate oocytes from a follicle;
    culturing in vitro the removed immature primate oocytes in a culture medium comprising human inhibin and human activin; wherein said human inhibin and said human activin are both present in an amount effective to increase the number of mature primate oocytes; and
    fertilizing the cultured primate oocytes to form a viable embryo.

13. The method of claim 12, wherein said fertilizing comprises mixing the cultured oocytes with spermatozoa.

14. The method of claim 12, wherein said fertilizing comprises injecting sperm into the cultured oocytes.

15. The method of claim 12, wherein said fertilizing takes place in vitro and the fertilized embryo is transferred to a female for development in utero.

16. A method for increasing the number of mature cryopreserved primate oocytes, comprising:
    cryopreserving immature primate oocytes;
    thawing the cryopreserved immature primate oocytes; and
    culturing in vitro the thawed immature primate oocytes in a culture medium comprising human inhibin and human activin to produce intact, viable primate oocytes capable of fertilization; wherein said human inhibin and said human activin are both present in an amount effective to increase the number of mature primate oocytes.

17. The method of claim 16, wherein said immature primate oocytes are removed from unstimulated ovaries.

18. The method of claim 16, further comprising fertilizing the cultured oocytes.

* * * * *